United States Patent
Melanson et al.

(10) Patent No.: US 6,610,033 B1
(45) Date of Patent: Aug. 26, 2003

(54) DUAL COMPONENT MEDICINAL POLYMER DELIVERY SYSTEM AND METHODS OF USE

(75) Inventors: David A. Melanson, Hudson, NH (US); Michelle D. Lyman, Peabody, MA (US); Peter G. Edelman, Franklin, MA (US); Amarpreet S. Sawhney, Lexington, MA (US)

(73) Assignee: Incept, LLC, Lexington, MA (US)

( * ) Notice: Subject to any disclaimer, the term of this patent is extended or adjusted under 35 U.S.C. 154(b) by 36 days.

(21) Appl. No.: 09/687,588

(22) Filed: Oct. 13, 2000

(51) Int. Cl.⁷ ............................................. A61M 5/00
(52) U.S. Cl. ................................. 604/181; 604/93.01
(58) Field of Search .......................... 604/82, 83, 84, 604/85, 92, 187, 252, 93.01; 606/92, 93, 94

(56) References Cited

U.S. PATENT DOCUMENTS

| | | | | |
|---|---|---|---|---|
| 4,328,802 A | * | 5/1982 | Curley et al. | 128/272.1 |
| 4,367,737 A | * | 1/1983 | Kozam et al. | 128/215 |
| 4,458,733 A | | 7/1984 | Lyons | 141/1 |
| 4,607,671 A | * | 8/1986 | Aalto et al. | 141/329 |
| 4,759,756 A | * | 7/1988 | Forman et al. | 604/413 |
| 5,171,220 A | * | 12/1992 | Morimoto | 604/88 |
| 5,411,499 A | * | 5/1995 | Dudar et al. | 604/411 |
| 5,464,396 A | * | 11/1995 | Barta et al. | 604/191 |
| 5,542,934 A | * | 8/1996 | Silver | 604/191 |
| 5,688,254 A | * | 11/1997 | Lopez et al. | 604/283 |
| 5,776,125 A | * | 7/1998 | Dudar et al. | 606/411 |
| 5,819,988 A | * | 10/1998 | Sawhney et al. | 222/137 |
| 5,846,233 A | * | 12/1998 | Liley et al. | 604/414 |
| 5,954,708 A | * | 9/1999 | Lopez et al. | 604/533 |
| 5,957,898 A | * | 9/1999 | Jepson et al. | 604/256 |
| 6,099,504 A | * | 8/2000 | Gross et al. | 604/140 |
| 6,113,571 A | * | 9/2000 | Zinger et al. | 604/82 |
| 6,116,900 A | * | 9/2000 | Ostler | 433/89 |
| 6,149,628 A | * | 11/2000 | Szapiro et al. | 604/191 |
| 6,234,994 B1 | * | 5/2001 | Zinger | 604/82 |
| 6,245,046 B1 | * | 6/2001 | Sibbitt | 604/191 |
| 6,290,101 B1 | * | 9/2001 | Chang | 222/137 |

OTHER PUBLICATIONS

Document No. 09/390,046 is an application number and cannot be listed on referrence sheet.

* cited by examiner

Primary Examiner—Henry Bennett
Assistant Examiner—Nihir Patel
(74) Attorney, Agent, or Firm—Patterson, Thuente, Skaar, & Christensen, P.A.

(57) ABSTRACT

The present invention provides apparatus and methods for making and using a medicinal polymer formed from two components. The apparatus includes a double syringe holder housing first and second syringes that is adapted to be coupled with a predetermined orientation to a double vial holder housing first and second vials. The double syringe holder and double vial holder have mating key features that prevent the first syringe from being coupled to the second vial and the second syringe from being coupled to the first vial. The apparatus also includes a delivery device having first and second inlet ports and a key feature that prevents the first syringe from being coupled to the second inlet port and the second syringe from being coupled to the first inlet port.

20 Claims, 3 Drawing Sheets

US 6,610,033 B1

DUAL COMPONENT MEDICINAL POLYMER DELIVERY SYSTEM AND METHODS OF USE

FIELD OF THE INVENTION

This invention relates to a kit and methods for reconstituting one or more dry powders with one or more liquids for use in a medical polymer delivery system. More particularly, this invention relates to a polymer kit and delivery system that prevents accidental blockage of the lumens of the delivery system due to mixing of precursor solutions within the device.

BACKGROUND OF THE INVENTION

Hydrogels are materials that absorb solvents (such as water), undergo rapid swelling without discernible dissolution, and maintain three-dimensional networks capable of reversible deformation. See, e.g., Park, et al., *Biodegradable Hydrogels for Drug Delivery*, Technomic Pub. Co., Lancaster, Pa (1993).

Hydrogels may be uncrosslinked or crosslinked. Crosslinking involves mixing two components (e.g., solutions) to form a hydrogel. Crosslinkable solutions used to form hydrogels include those that may be used to form coatings on tissue, and may form physical crosslinks, chemical crosslinks, or both. Physical crosslinks may result from complexation, hydrogen bonding, desolvation, Van der Waals interactions, ionic bonding, etc., and may be initiated by mixing two components that are physically separated until combined in situ, or as a consequence of a prevalent condition in the physiological environment, such as temperature, pH, ionic strength, etc. Chemical crosslinking may be accomplished by any of a number of mechanisms, including free radical polymerization, condensation polymerization, anionic or cationic polymerization, step growth polymerization, etc.

For example, commonly owned U.S. patent application Ser. No. 09/390,046 describes a system for forming a hydrogel using two components that are separately introduced and mixed in situ from two syringes. Each of the two components is separately applied from a syringe into a respective lumen of a multi-lumen device that transports the components separately to the tissue site to be treated. The two components mix when released from the distal end of the device and combine in situ to form the desired hydrogel.

Several systems are known for reconstituting pharmaceutical or medicinal agents that need to be stored in a dry configuration and then are mixed with an aqueous solution prior to use, such as described in U.S. Pat. Nos. 4,458,733, 4,607,671, 4,759,756, and 4,328,802. For example, pre-filled syringes containing aqueous buffers are routinely used to reconstitute lyophilized drug or pharmaceutical powders in medical practice, such as described in U.S. Pat. No. 6,099,504, where the powders are stored dry for enhanced shelf life. In addition, the use of needle-less connectors are known for use in such systems, to minimize injuries, as described, for example, in U.S. Pat. Nos. 5,411,499, 5,688,254, 5,776,125, 5,846,233, 5,954,708, and 5,957,898. Several syringe configurations also are known in which a dry powder and a liquid component are separated by a barrier that allows intermixing prior to use, such as described in U.S. Pat. No. 5,171,220.

None of these systems, however, are suitable for use in dual component systems where two liquids are being used to simultaneously reconstitute two dry ingredients. In particular, the extension of single systems to dual systems is non-trivial because pre-configuration of the two liquid syringes can prevent the luer-locking mechanism from being engaged unless specific design features enable such movement. Additionally, there are unanticipated benefits of having a pre-configured system that arranges the two syringes in a rigid configuration relative to each other because such an arrangement obviates the need to separately level the liquid levels of the two syringes prior to introducing the liquids into the two dry powders. Accordingly, the quantities being thus introduced are uniform and assured to be in appropriate proportions.

Several dual component based medically useful polymer formulations are known in the art or are being developed. For example, fibrin sealants use a mixture of thrombin and fibrinogen based solutions to form fibrin glue and have numerous therapeutic uses. Similarly, several synthetic biomaterials based on polymers such as polyethylene glycol (PEG) are being developed. In general there is a need to store at least one if not both of the components of these dual component systems in a dry form that is reconstituted prior to use, for example in an operating room prior to surgery. However, this process for reconstitution can be time consuming and cumbersome. For example, the process for preparation of fibrin sealants involves more than a dozen steps to form a usable product and the process itself can take up to 45 minutes.

Where two liquids are used to reconstitute two dry powders, the liquids often are incompatible with the other dry powder and there is the possibility of accidentally mixing the wrong liquid with dry powder of the other liquid.

Moreover, additional applications of the two components from the syringes into the delivery device may be required to form a sufficient amount of polymer, such as a hydrogel. However, if the two components are applied to different lumens in subsequent applications such that portions of the two components from different applications mix inside the lumens, the polymer may form in the delivery device, thus causing the lumens to become blocked.

Additionally, it may be desirable to include one or more of a variety of drugs or bioactive agents in one or both of the polymer components, but not until shortly before it is desired to employ the components.

It would therefore be desirable to provide a simple, error-proof kit and system to rapidly prepare dual component systems.

It also would be desirable to provide methods and apparatus that prevents the lumens used to transport polymer components from becoming blocked by ensuring that the components do not become mixed inside the lumens of the delivery device during repeated applications of the components with the delivery device.

It further would be desirable to prevent blockage in lumens used to transport polymer components by providing a kit and delivery system having a key feature that prevents more than one type of polymer component from being applied inside a given lumen of the delivery device.

It still further would be desirable to provide a multi-component polymer kit and delivery system in which one or both components may include any one of a variety of drugs or biactive agents in either liquid or powder form.

SUMMARY OF THE INVENTION

In view of the foregoing, it is an object of the present invention to provide a simple, error-proof kit and system to rapidly prepare dual component medicinal polymer systems.

It is another object of the present invention to provide methods and apparatus that prevents the lumens used to transport polymer components from becoming blocked by ensuring that the components do not become mixed inside the lumens of the delivery device during repeated applications of the components with the delivery device.

It is a further object of the invention to prevent blockage in lumens used to transport polymer components by providing a kit and delivery system having a key feature that prevents more than one type of component from being applied inside a given lumen of the delivery device.

It is yet another object of the present invention to provide a multi-component polymer kit and delivery system in which one or both components may include any one of a variety of drugs or biactive agents in either liquid or powder form.

These and other objects of the invention are accomplished by providing a kit and delivery system having a key feature, and methods of use, that ensure proper mixing of the liquids and dry powders used to from the polymer components, and that prevent blockage of the delivery system lumens used to transport the components to the target site.

In a preferred embodiment, the two liquids are contained in pre-filled containers, such as syringes that are mounted in a clip that holds the syringes in a pre-determined configuration. A rigid member is removably coupled to the plungers of the syringes to allow simultaneous advancement of both plungers. Two substantially dry powders are disposed within containers, such as vials, and are also optionally mounted in a clip that is configured to allow for simultaneous attachment of both containers or vials of dry powders to be attached to the pre-filled syringes containing the liquids in a predetermined orientation. Needle-less connectors preferably are used to provide a continuous pathway allowing the liquids to flow from the pre-filled syringes into the respective vials containing the dry powders.

Once the double syringe holder is coupled to the double vial holder, the rigid member is advanced to simultaneously introduce the liquids into the respective vials containing the dry powders. The powders mix with the liquids to form the polymer components, which are then withdrawn from the vials into the syringes. The double syringe holder includes a key features that mates with a corresponding key feature of the double vial holder, thereby permitting the two elements to be coupled together with a predetermined orientation, so that the contents of each syringe can only be introduced into a corresponding one of the vials, but not the other vial. This ensures that each of the polymer components has the same orientation with respect to the syringes during repeated couplings of the syringes with the vials.

A delivery system is also provided that can be coupled to the double syringe holder with only one pre-determined orientation. Preferably, the delivery system includes multiple lumens. The double syringe holder is coupled to the delivery device so that the outlet of each syringe can be coupled to only a pre-selected one of the inlet ports of the delivery device. In this way each component is introduced into a separate lumen of the delivery device.

In accordance with the principles of the present invention, the delivery device also contains a key feature that permits the double syringe holder to be coupled in a unique configuration with a mating key feature of the delivery system. The key features therefore ensure that each of the polymer components is introduced through the same lumen upon repeated applications of the components to the delivery device. This in turn prevents accidental mixing of different components in the transport lumens, and thus prevents inadvertent blockage of the delivery device.

In addition, the kit and delivery system of the present invention facilitate use of one or more of a variety of drugs or bioactive agents as either the liquid or powder used in one or both of the polymer components.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
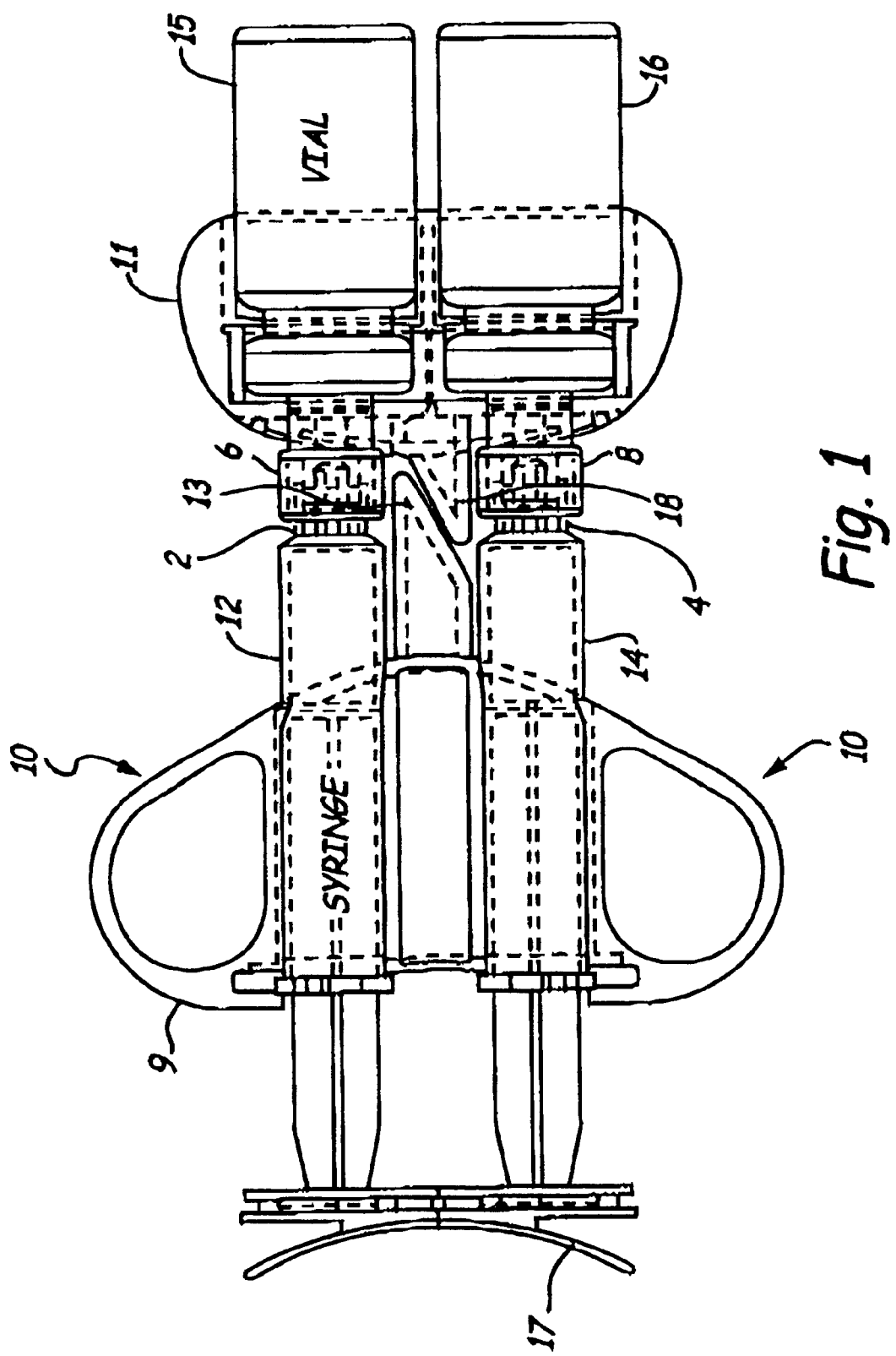
FIG. 1 is a plan view of a kit constructed in accordance with the principles of the present invention in which a double syringe holder having a key feature and two syringes is coupled to a double vial holder having a mating key feature and two vials.
Figure 2A:
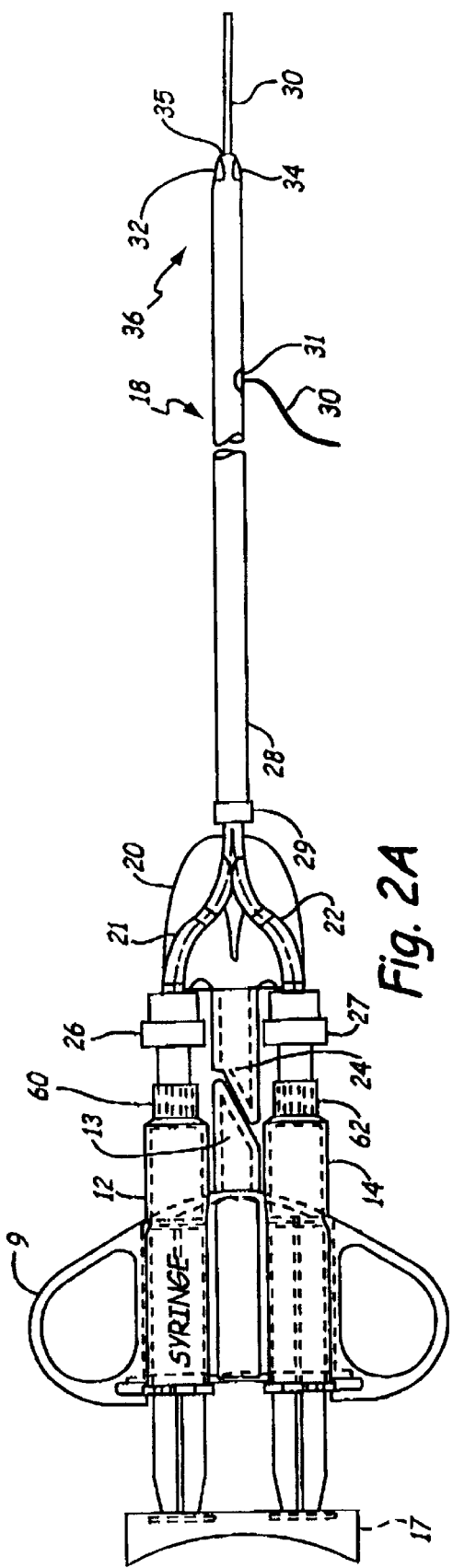
FIG. 2A is a depiction of a delivery system constructed in accordance with the principles of the present invention in which the double syringe holder is coupled to a delivery device.
Figure 2B:
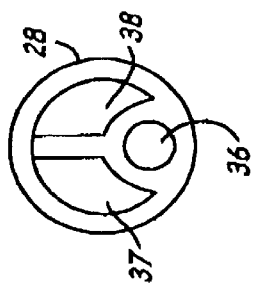
FIG. 2B is a depiction of a cross section of the delivery device of FIG. 2A.

The present invention provides a kit and delivery system for a polymer system comprising two components, where each component is formed from a liquid and a dry powder prior that are mixed shortly before use. The components of the polymer system may comprise, for example, fibrinogen and thrombin, or may be fully synthetic, such as a polyethylene glycol amine and a polyethylene glycol ester.

The liquids are stored in containers having the form of vials or more preferably, syringes. A double syringe holder is provided that enables the syringes to be snap-fit into the holder, and which is designed to permit the syringes to rotate independently without interfering with one another. End caps are placed on the liquid filled syringes to protect against spillage. A rigid member is removable attached to the plungers of both syringed to be allow simultaneous advancement of the plungers. Optionally, the rigid member may be removed where it is desired to advance only the plunger in one syringe, but not the other.

The dry powders also are stored in containers such as syringes, or more preferably, having the form of vials. For purposes of distinguishing this double container holder from the double syringe holder, the term "vial" is used herein as representative of any form of container for holding a substance, including syringes and ampules. These vials or containers as disposed in a double vial holder that accepts the double syringe holder in a predetermined orientation so that the contents of each syringe can be introduced into only one of the vials coupled to the double vial holder.

Preferably, the pre-filled syringes are coupled to the vials containing the dry powders using needle-less vial adapters formed, for example, from plastic materials such as polycarbonate. These adapters are mounted at the ends of the syringes and snap fit onto the vials containing the dry powders. Such vial caps are commercially available from Becton-Dickinson, Inc., Franklin Lakes, N.J., and enable the creation of a communication channel between a vial containing a dry powder and a liquid-filled syringe by mounting the syringe on a luer adapter on the vial cap, without the use of a needle.

In accordance with the principles of the present invention, the double syringe holder includes a key feature that mates with a corresponding key feature of the double vial holder to allow these elements to be coupled in only one orientation to minimize or eliminate potential cross contamination of the liquids from the pre-filled syringes during the reconstitution process. Once both vials have been mounted at the end of both syringes, the plungers are advanced by pushing on the rigid connecting member, thereby causing the liquids to be introduced into the vials and solubilize of the dry powders. Additional "pumping" of the connected plungers, or agitation of the vials, can expedite the dissolution process.

Once complete dissolution of the dry powders is attained, the solutions are withdrawn into the syringes and the vials are disconnected from the syringes. In a preferred arrangement, the needle-less vial adapters remain with the vial set and so do not present any hazard and minimize waste components during the reconstitution process. The reconstituted solutions then are used for the intended medically useful purpose. Optionally, one or both or the liquids or powders may include one or more of a variety of drugs or bioactive agents, i.e., genes, to enhance the diagnostic or therapeutic effect of the polymer when deployed in-situ.

The kit, consisting of the syringes, the syringe handle, the vial set, and the needle-less connectors preferably is placed within a molded plastic tray or other packaging that maintains the components in a configuration facilitating the reconstitution. Additional protective packaging also may be used. The kit can be sterilized using one of several techniques known in the art, including but not limited to ethylene oxide, peroxide plasma, electron beam, autoclaving, and radiation. The kit also may be assembled using aseptic technique.

Referring now to FIG. 1, an illustrative embodiment of a kit constructed in accordance with the present invention is described for use in mixing and delivering a biodegradable hydrogel. Double syringe holder 9 is depicted coupled to double vial holder 11. Two syringes, 12 and 14, are disposed within double syringe holder 9, while two vials, 15 and vial 16, are disposed within double vial holder 11. Syringe 12 preferably is pre-filled with a first liquid, which when mixed with a substantially dry powder in vial 15, forms a first component. Syringe 14 also preferably is pre-filled with a second liquid, which when mixed with a substantially dry powder in vial 16, forms a second component. The hydrogel is formed when the first and second components or "precursor solutions" are combined in situ using a delivery device, as described hereinbelow.

Double syringe holder 9 contains two handle portions 10 for grasping double syringe holder 9 and actuating syringes 12 and 14. Vial 15 has an inlet port in lid portion 6, and vial 16 has an inlet port in lid portion 8. Double syringe holder 9 is used to couple syringes 12 and 14 with inlet ports 6 and 8 of vials 15 and 16 via connectors 2 and 4. Once syringes 12 and 14 are coupled to vials 15 and 16 via connectors 2 and 4, respectively, actuator 17 is advanced (i.e., moved to the right in FIG. 1) so that the first and second liquids in syringes 12 and 14 are introduced into vials 15 and 16, respectively. The powders mix with the liquids in the vials tom form the components, which are then withdrawn into syringes 12 and 14 by retracting actuator.

In accordance with the principles of the present invention, double syringe holder 9 contains key feature 13, and double vial holder 11 contains mating key feature 18. Illustratively, key feature 13 has a triangular profile (when viewed from the side as in FIG. 1), while key feature 18 has a mating triangular profile. Key features 13 and 18 only fit together with a single pre-determined orientation, as shown for example, in FIG. 1. Accordingly, syringe 12 can only be coupled to vial 15, and syringe 14 can only be coupled to vial 16.

As will be apparent from inspection of FIG. 1, double syringe holder 9 cannot be coupled to double vial holder 11 is one element is rotated 180° about a longitudinal axis relative to the other. Key features 13 and 18 thereby ensure that the liquid in syringe 12, which is used to reconstitute the first component, cannot accidentally be introduced into vial 16, and that the liquid in syringe 14 cannot be introduced into vial 15.

Referring to FIG. 2A, double syringe holder 9 is shown coupled to illustrative delivery device 18 constructed in accordance with the principles of the present invention. Delivery device 18 includes proximal end 20, multi-lumen catheter 28 and distal end 36 having outlet ports 32 and 34. Proximal end 20 of delivery device 18 includes inlet ports 26 and 27, and key feature 24.

Syringes 12 and 14 of double syringe holder 9 are respectively coupled to inlet ports 26 and 27 via connectors 60 and 62 to provide the first and second components through multi-lumen catheter 28 to outlet ports 32 and 34, respectively. In particular, advancement of actuator 17 causes the first and second components to be injected into lumens 21 and 22, respectively, of device 18. Proximal end 20 is coupled to catheter 28 via connector 29, or alternatively is integrally formed with catheter 28. Preferably, the first and second components are kept separate from one another in separate lumens inside catheter 28, and do not mix together until expelled through outlet ports 32 and 34 at the tissue treatment site.

Without key feature 24, the first component could accidentally be mixed with the second component within the lumens of catheter 28 where repeated applications of the first and second components to device 18 are required. This could in turn caused the hydrogel to form within the lumens of the catheter, blocking delivery of the components to target tissue site through outlet ports 32 and 34.

Key feature 24, however, prevents such inadvertent mixing, by requiring that the double syringe holder be coupled to the proximal end of device 18 with a predetermined orientation. Key features 13 and 24 therefore prevent the first and second components from being accidentally injected into different lumens 21 and 22 upon repeated applications of the components to device 18.

Multi-lumen catheter 28 preferably has distal end 36 having a guidewire lumen extending between lateral skive 31 and guidewire port 35 to permit guidewire 30 to be extended through the guide wire lumen is a rapid exchange manner. Guidewire 30 advantageously may be used to position device 28 at a treatment site, such as a fallopian tube or a peripheral or coronary artery. As illustrated in FIG. 2B, device 28 preferably includes lumens 36, 37, and 38. Lumen 37 couples inlet port 26 to outlet port 32, lumen 38 coupled inlet port 27 to outlet port 34, and lumen 36 couples lateral skive 31 to guidewire port 35.

In operation, lumen 36 is used to position the catheter 28 at a desired position within a vessel or organ. After reconstituting the first and second components from the liquids in syringes 12 and 14 and vials 15 and 16, and or adding any desired drugs, double syringe holder 9 is coupled to proximal end 20 of device 18. Actuator 17 is then advanced to inject the first component through lumens 21 and lumen 37 while the second component is injected through lumens 22 and lumen 38. The components exit lumens 37 and 38 at the target tissue site through outlet ports 32 and 34, where the components mix and crosslink to form a hydrogel implant.

Figure 3A:
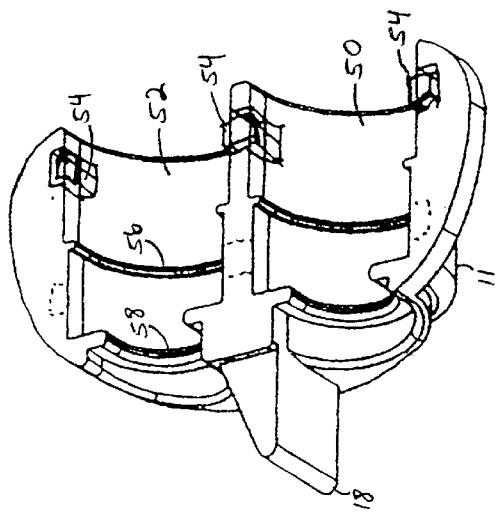
FIGS. 3A and 3B are, respectively, a perspective view of a double syringe holder and a double vial holder constructed in accordance with the present invention and a partial cross section of the double syringe holder of FIG. 3A.
Figure 3B:
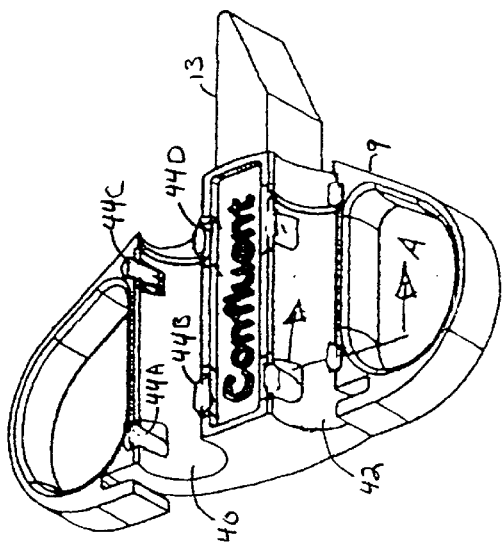
Figure 3B:
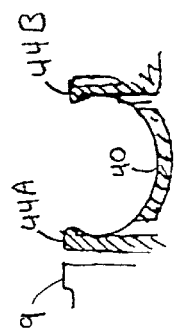

FIGS. 3A and 3B provide additional views of double syringe holder 9 (without syringes 12 and 14) and double vial holder 11 (without vials 15 and 16). Preferably, double syringe holder 9 has grooves 40 and 42 for accepting syringes 12 and 14, respectively. Resilient clips 44A, 44B, 44C, and 44D protrude through corresponding holes in the edges of groove 40 as shown in FIG. 3A. Clips 44A–44D are bendable outward with respect to the center of groove 40, so as to expand radially outward to accept syringe 12 and retain it firmly in place within groove 40. Identical clips protrude through the holes in the edges of groove 42 to firmly retain syringe 14 within groove 42.

FIG. 3B depicts a cross sectional view of double syringe holder 9 taken along longitudinal axis A, illustrating the location of clips 44A and 44B. Clips 44A–44D preferably are connected to one another underneath groove 40, so that clips 44A–44D may be inserted into and removed from double syringe holder 9 as a unit. The four clips along the edges of groove 42 may also be connected underneath groove 42.

Double vial holder 11 also includes grooves 50 and 52 that accept vials 15 and 16, respectively. Resilient clips 54 protrude through holes in the edges of grooves 52 and 50, and are bendable to allow vials 15 and 16 to be accepted into, and retained within, grooves 52 and 50, respectively. Clips 54 may be connected together underneath grooves 52 and 50, so that they can be inserted into and removed from double vial holder 11 as a unit. Grooves 50 and 52 of double vial holder 11 also each contain ring protrusions 56 and 58 that engage neck portions of the respective vials 15 and 16 and assist in retaining the vials within grooves 52 and 50.

The foregoing is merely illustrative of the principles of this invention and various modifications can be made by those skilled in the art without departing from the scope and spirit of the invention.

What is claimed is:

1. Apparatus for reconstituting and using a medicinal polymer from first and second components, the apparatus comprising:
    a double syringe holder having a first key feature and housing first and second syringes; and
    a double vial holder comprising a second key feature and housing first and second vials,
    the second key feature adapted to mate with the first key feature with a predetermined orientation;
    with the first and the second components of the medicinal polymer being disposed in at least one member of the group consisting of the vials and the syringes; and
    connectors for coupling the first and second syringes to the first and second vials, respectively, when the first key feature mates to the second key feature.

2. The apparatus of claim 1 further comprising a delivery device, the delivery device comprising a third key feature adapted to mate with the first key feature with a predetermined orientation.

3. The apparatus of claim 2 wherein the delivery device further comprises first and second inlet ports, the first and second inlet ports coupling to the first and second syringes, respectively, when the first key feature mates to the third key feature.

4. The apparatus of claim 1 wherein the double syringe holder further comprises a handle portion.

5. The apparatus of claim 1 wherein the double syringe holder further comprises a first groove and a second groove and wherein the first syringe is disposed within the first groove and the second syringe is disposed within the second groove.

6. The apparatus of claim 5 wherein the double syringe holder further comprises:
    a first plurality of clips protruding through a first plurality of holes in the first groove to retain the first syringe in the first groove; and
    a second plurality of clips protruding through a second plurality of holes in the second groove to retain the second syringe in the second groove.

7. The apparatus of claim 1 wherein the double vial holder further comprises a first groove for retaining the first vial and a second groove for retaining the second vial.

8. The apparatus of claim 7 wherein the double vial holder further comprises:
    a plurality of clips protruding through a plurality of holes in the first and second grooves to retain the first and second vials in the first and second grooves, respectively.

9. The apparatus of claim 2 wherein the delivery device further comprises first and second lumens coupled to the first and second inlet ports, respectively.

10. The apparatus of claim 9 wherein the delivery device includes first and second outlet ports, the first and second outlet ports coupled to the first and second lumens, respectively.

11. A method for making and delivering first and second components that form a medicinal polymer, the method comprising:
    providing a double syringe holder having a first key feature and housing first and second syringes;
    providing a double vial holder housing first and second vials;
    placing the first component and the second component into separate vials or syringes; and
    coupling the double syringe holder to the double vial holder via a second key feature adapted to mate with a first key feature with a predetermined orientation so that the first syringe couples to the first vial and the second syringe couples to the second vial.

12. The method of claim 11 further comprising:
    actuating the first and second syringes to introduce the first liquid into the first vial and the second liquid into the second vial; and
    after the first liquid dissolves the first powder to form a first component and the second dissolves the second powder to form a second component, actuating the first and second syringes to withdraw the first component into the first syringe and the second component into the second syringe.

13. The method of claim 12 further comprising, prior to actuating the first and second syringes to withdraw the first and second components, agitating the first and second vials.

14. The method of claim 12 further comprising connecting a delivery device with a predetermined orientation by uncoupling the double syringe holder from the double vial holder, and coupling the double syringe holder to the delivery device with a predetermined orientation.

15. The method of claim 14 further comprising actuating the first and second syringes to introduce the first and second components through the delivery device to a target site.

16. The method of claim 15 further comprising positioning a distal end of the delivery device at a target site by advancing the distal end of the delivery device along a guidewire.

17. The method of claim 11 wherein providing a double syringe holder further comprises inserting a first syringe into a first groove of the double syringe holder and inserting a second syringe into a second groove of the double syringe holder.

18. The method of claim 17 wherein inserting a first syringe into a first groove of the double syringe holder comprises actuating a first plurality of clips protruding through a first plurality of holes in the first groove, and inserting a second syringe into the second groove of the double syringe holder comprised actuating a second plurality of clips protruding through a second plurality of holes in the second groove.

19. The method of claim 11 wherein providing a double vial holder further comprises inserting a first vial into a first groove of the double vial holder and inserting a second vial into a second groove of the double vial holder.

20. The method of claim 19 wherein inserting the first and second vials into the first and second grooves, respectively, further comprises actuating a plurality of clips protruding through a plurality of holes in the first and second grooves of the double vial holder.

* * * * *

UNITED STATES PATENT AND TRADEMARK OFFICE
CERTIFICATE OF CORRECTION

PATENT NO. : 6,610,033 B1
DATED : August 26, 2003
INVENTOR(S) : David A. Melanson et al.

It is certified that error appears in the above-identified patent and that said Letters Patent is hereby corrected as shown below:

<u>Column 5,</u>
Line 64, please delete "tom" and insert -- to --.
Line 65, after "actuator" insert -- 17 --.

<u>Column 7,</u>
Line 52, after "orientation" insert -- so that the contents of each syringe can only be introduced into a corresponding one of the vials, but not the other --.

<u>Column 8,</u>
Lines 45-46, please delete "first syringe couples to the first vial and the second syringe couples to the second vial" and insert -- contents of each syringe can only be introduced into a corresponding one of the vials, but not the other --.
Line 53, please indent "actuating the first and second syringes to withdraw the first component into the first syringe and the second component into the second syringe".

<u>Column 9,</u>
Line 13, after "of" insert -- clips of --.

Signed and Sealed this

Sixth Day of April, 2004

JON W. DUDAS
*Acting Director of the United States Patent and Trademark Office*